(12) United States Patent
Chan et al.

(10) Patent No.: US 6,547,807 B2
(45) Date of Patent: Apr. 15, 2003

(54) SUTURE RELAY FOR SURGERY

(76) Inventors: Kwan-Ho Chan, 4803 1st Pl., Lubbock, TX (US) 79416; Mark A. Johanson, 5 Harvest La., Littleton, MA (US) 01460; Dennis McDevitt, 2 Nathaniel Way, Upton, MA (US) 01568; Vince Novak, 24 Madeline Dr., Groton, MA (US) 01450

( * ) Notice: Subject to any disclaimer, the term of this patent is extended or adjusted under 35 U.S.C. 154(b) by 0 days.

(21) Appl. No.: 09/728,177

(22) Filed: Dec. 1, 2000

(65) Prior Publication Data

US 2001/0049536 A1 Dec. 6, 2001

Related U.S. Application Data

(60) Provisional application No. 60/168,891, filed on Dec. 3, 1999.

(51) Int. Cl.[7] .............................................. A61L 17/00
(52) U.S. Cl. ...................... 606/228; 606/145; 606/139
(58) Field of Search ................................ 606/228, 139, 606/144, 148, 185, 187, 222, 223, 224; 128/898

(56) References Cited

U.S. PATENT DOCUMENTS

| | | | | | |
|---|---|---|---|---|---|
| 4,971,075 | A | * | 11/1990 | Lee .............................. | 128/898 |
| 5,250,053 | A | * | 10/1993 | Snyder ......................... | 606/145 |
| 5,279,311 | A | * | 1/1994 | Snyder ......................... | 128/898 |
| 5,282,809 | A | * | 2/1994 | Kammerer et al. .......... | 606/148 |
| 5,562,687 | A | * | 10/1996 | Chan ............................ | 606/148 |
| 5,681,333 | A | * | 10/1997 | Burkhart et al. ............. | 606/148 |
| 5,746,752 | A | * | 5/1998 | Burkhart ...................... | 606/139 |
| 5,746,754 | A | * | 5/1998 | Chan ............................ | 606/148 |
| 5,776,151 | A | * | 7/1998 | Chan ............................ | 606/148 |
| 5,782,864 | A | * | 7/1998 | Lizardi ......................... | 606/232 |
| 6,206,886 | B1 | * | 3/2001 | Bennett ........................ | 606/104 |
| 6,368,335 | B1 | * | 4/2002 | Chan ............................ | 606/146 |

* cited by examiner

*Primary Examiner*—John J. Calvert
*Assistant Examiner*—Alissa L. Hoey
(74) *Attorney, Agent, or Firm*—Pandiscio & Pandiscio

(57) ABSTRACT

A suture relay that can be advanced, by pushing, through the hollow needle of a suture passer and which is adapted to carry a braided suture across the tissue.

12 Claims, 3 Drawing Sheets

The two loops are engaged

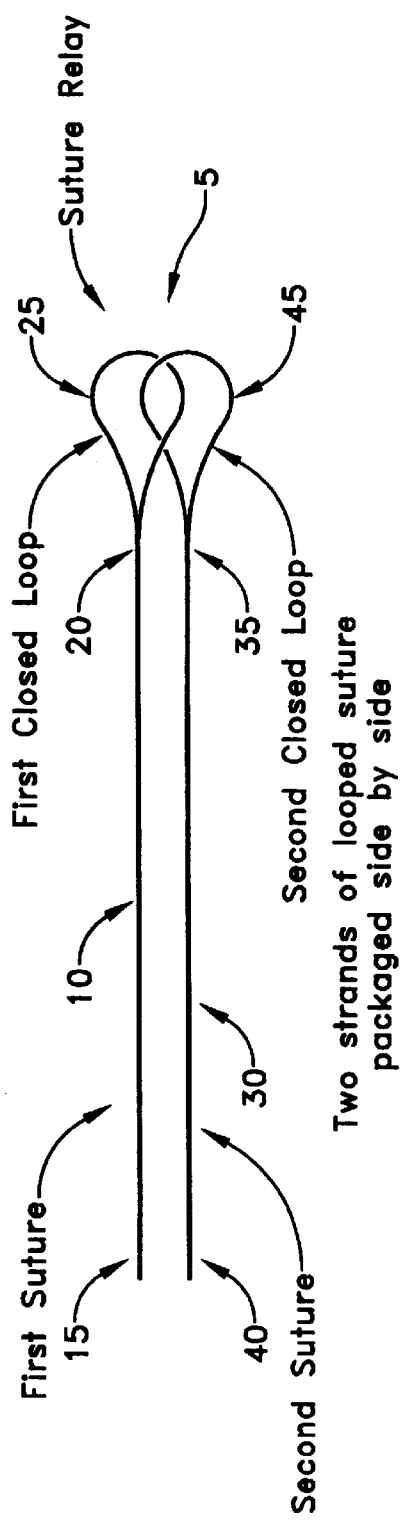
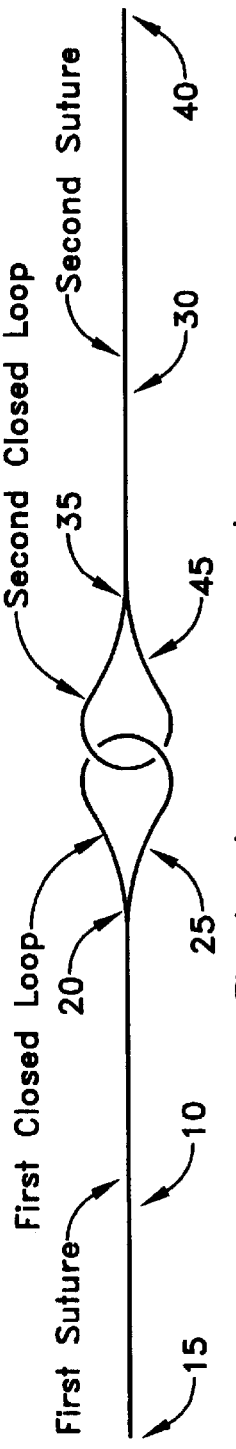
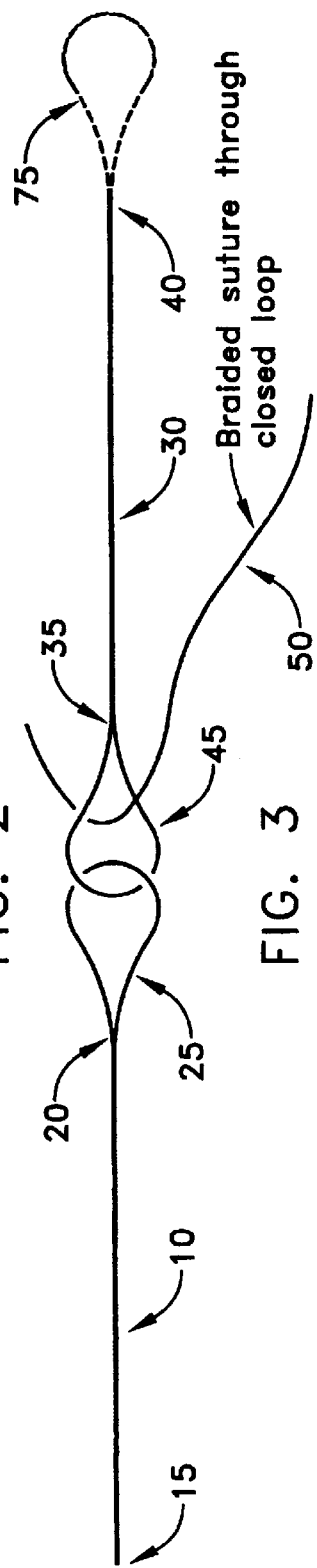

SUTURE RELAY FOR SURGERY

REFERENCE TO PENDING PRIOR PATENT APPLICATION

This patent application claims benefit of now abandoned prior U.S. Provisional Patent Application Serial No. 60/168, 891, filed Dec. 3, 1999 by Kwan-Ho Chan for SUTURE RELAY FOR SURGERY, which patent application is hereby incorporated herein by reference.

FIELD OF THE INVENTION

The present invention relates to medical devices for performing surgery and to surgical repair kits containing the same. More particularly, the present invention is directed to a surgical repair kit useful for transporting suture during arthroscopic rotator cuff repairs, arthroscopic shoulder stabilization surgeries, arthroscopic meniscal repairs and other surgical procedures.

BACKGROUND OF THE INVENTION

A group of four muscles around the shoulder joint is called the rotator muscles of the shoulder. The tendonous portions of those muscles that insert into the bony tuberosities of the humeral head are known as the rotator cuffs. The rotator cuffs are frequently torn at, or close to, the point of bony insertion due to trauma or due to degenerative changes frequently associated with aging. Weakness and pain are common indications for the surgical repair of rotator cuffs. The surgical procedure consists of the reattachment of the rotator cuff to its bony bed.

Another type of tear in the shoulder that frequently requires surgical intervention relates to instability of the shoulder joint after the shoulder has been previously dislocated. This instability is commonly the result of a tearing of the joint capsule and its labrum (a fibrocartilaginous structure) from the anterior aspect of the glenoid. This deficiency is commonly referred to as a Bankart lesion. One procedure for correcting the instability associated with a Bankart lesion is to reattach the torn capsule and labrum to bone on the anterior aspect of the glenoid.

Both of the aforementioned procedures, as well as many others, involve the reattachment of soft tissue to bone.

The widespread adoption of the arthroscope has made it possible for the surgeon to visualize the interior of the joint and to perform surgery through small puncture holes without having to lay open the joint as was previously necessary. In addition, the advent of suture anchors, and associated instrumentation, has made it possible for surgeons skilled in arthroscopy to perform the two aforementioned procedures, and others, arthroscopically.

Other arthroscopic procedures include the repair of the meniscus, such as is disclosed in U.S. Pat. No. 5,776,151, issued Jul. 7, 1998 to Kwan-Ho Chan for SURGICAL REPAIR KIT AND ITS METHOD OF USE, which patent is hereby incorporated herein by reference.

The basic steps in arthroscopic rotator cuff repair and in arthroscopic Bankart repair involve:

(1) embedding a suture anchor in a bony bed;
(2) passing a suture (attached to the embedded suture anchor) through the soft tissue which is to be reattached to the bony bed; and
(3) tying the soft tissue to the suture anchor, thus coapting the torn tissue to the bony bed.

At other times, torn or lax tissues are repaired or tightened by passing sutures through two points in the soft tissue and then tying them together.

A number of surgical instruments have been developed to assist in suturing in general and, in particular, in the suturing of soft tissue arthroscopically.

One such surgical instrument, sometimes referred to as a suture passer, comprises a hollow needle for penetrating tissue. One such suture passer is disclosed in the aforementioned U.S. Pat. No. 5,776,151, which has already been incorporated herein by reference. Another such suture passer is disclosed in pending U.S. patent application Ser. No. 09/400,162, filed Sep. 21, 1999 by Kwan-Ho Chan for SURGICAL REPAIR KIT AND ITS METHOD OF USE, which patent application is hereby incorporated herein by reference.

In use, the hollow needle of the suture passer is advanced through the soft tissue; suture is then advanced through the hollow needle and hence through the soft tissue. To advance the suture through the hollow needle, the suture is pushed forward from the proximal end of the instrument.

This technique generally works well where the suture comprises a relatively stiff element, e.g., monofilament suture. However, where the suture comprises a relatively limp element, such as braided suture, the suture will tend to buckle when the surgeon attempts to push it forward.

Thus, when using a suture passer of the type described above, monofilament suture is typically the suture of choice, since such suture can be pushed forward without excessive buckling.

However, at times it may be desirable to use a braided suture such as Ethibond™ suture, because of certain attributes of the suture material (such as superior knot security, the non-absorble nature of the material, etc.). Unfortunately, this is currently not possible with suture passers of the type described above.

Therefore, the need exists for an improved method and apparatus for passing braided suture and the like through a suture passer.

SUMMARY OF THE INVENTION

In accordance with the present invention, there is provided an improved method and apparatus for advancing braided suture through a suture passer. In one preferred embodiment, the invention comprises a suture relay that can be advanced, by pushing, through the suture passer and which is adapted to carry a braided suture across the tissue.

BRIEF DESCRIPTION OF THE DRAWINGS

These and other objects and features of the present invention will be more fully disclosed or rendered obvious by the following detailed description of the preferred embodiments, which is to be considered together with the accompanying drawings wherein:

FIG. 1 is a schematic view showing one form of the suture relay, wherein the suture relay comprises a pair of sutures, with each suture having a closed loop at one end thereof, and further wherein the closed loops are engaged with one another, with the suture relay being shown ready for packaging, with the two sutures being disposed alongside one another;

FIG. 2 is a schematic view showing the suture relay of FIG. 1, with the suture relay being prepared for use by positioning its two sutures in series with one another;

FIG. 3 is a schematic view of the suture relay of FIGS. 1 and 2, with a passenger suture being shown inserted through one of the suture relay's loops;

DETAILED DESCRIPTION OF THE PREFERRED EMBODIMENT

Figure 4:
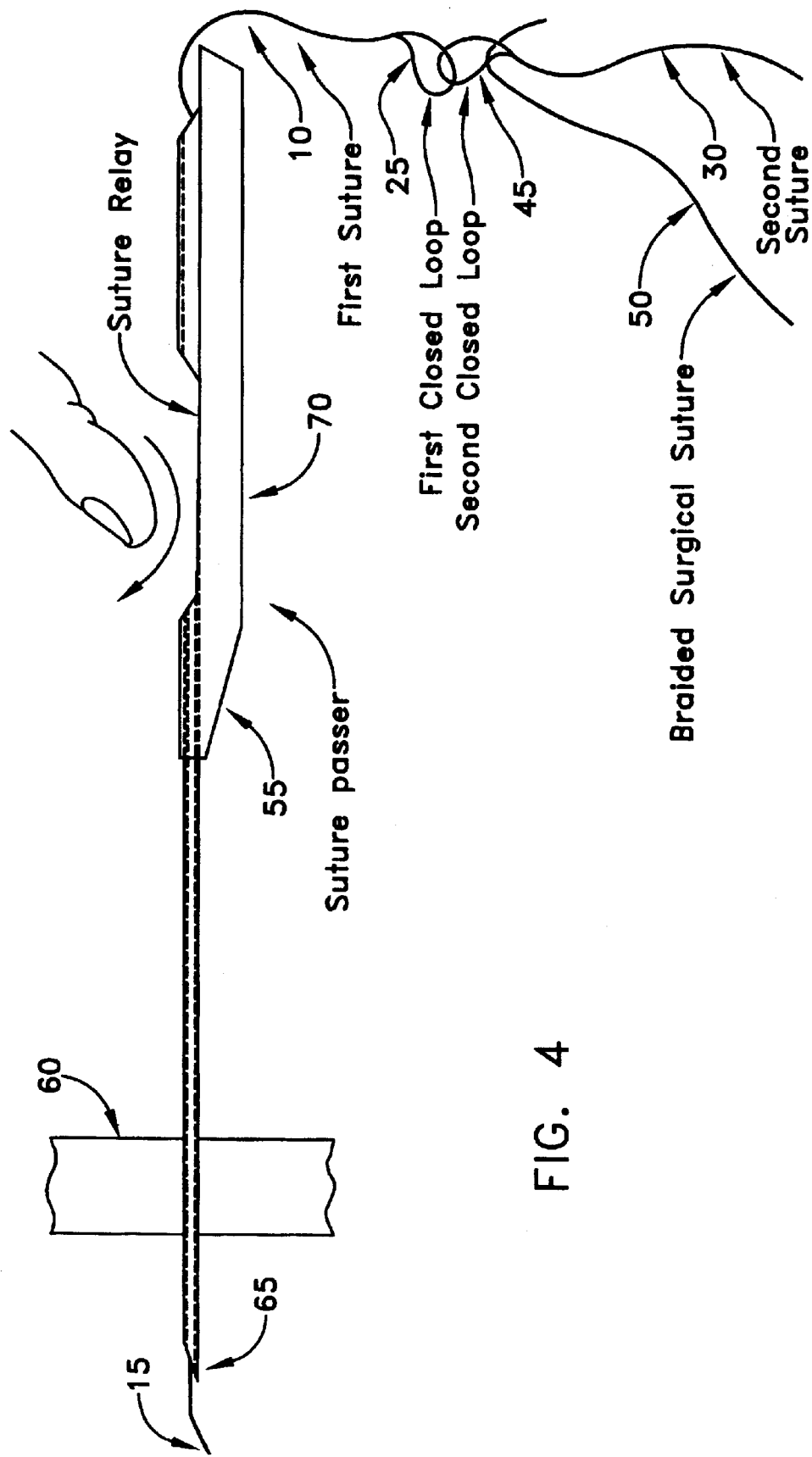
FIG. 4 is a schematic view showing the suture relay and passenger suture of FIG. 3 being loaded through a suture passer.

Looking first at FIG. 1, there is shown a suture relay 5 which comprises a preferred form of the invention.

Suture relay 5 generally comprises a first suture 10 having a distal end 15 and a proximal end 20, with a closed loop 25 being formed at proximal end 20.

Suture relay 5 also comprises a second suture 30 having a distal end 35 and a proximal end 40, with a closed loop 45 being formed at distal end 35.

The closed loop 25 of first suture 10 is engaged with the closed loop 45 of second suture 30, so that the two sutures are connected to one another.

First suture 10 and second suture 30 are formed out of a relatively stiff material, e.g., monofilament suture, such that they may be pushed through a suture passer, as will hereinafter be discussed.

Suture relay 5 is preferably packed with first suture 10 and second suture 30 disposed alongside one another, in the manner shown in FIG. 1.

In use, the suture relay is first prepared by positioning first suture 10 and second suture 30 in series, in the manner shown in FIG. 2. Then a passenger suture 50 (FIG. 3) inserted through one of the suture relay's loops, i.e., it is inserted through closed loop 25 or closed loop 45, in the manner shown in FIG. 3. Then a suture passer 55 (FIG. 4), such as one disclosed in the aforementioned U.S. Pat. No. 5,776,151 or the aforementioned pending U.S. patent application Ser. No. 09/400,162, both of which have already been incorporated herein by reference, is passed through a piece of tissue 60 so that the distal end 65 of the suture passer is located on one side of the tissue and its handle 70 is located on the other side of the tissue. Then the distal end 15 of first suture 10, which is preferably a relatively stiff suture such as monofilament suture, is inserted into the handle side of the suture passer and pushed distally. As this occurs, the passenger suture 50, which is preferably a relatively limp suture such as braided suture, is pulled through the suture passer and hence through the tissue. In this way a relatively limp braided suture may be passed through a hollow suture passer and hence through a piece of tissue.

Additionally, an alternative method of using the suture relay includes positioning first suture 10 and second suture 30 in series, in the manner shown in FIG. 2. Then suture passer 55 is passed through a piece of tissue 60 so that the distal end 65 of the suture passer is located on a distal side of the tissue and its handle 70 is located on a proximal side of the tissue. Then the distal end of first suture 10 is inserted into the handle side of the suture passer and pushed distally. After one or more of the suture relay's loops is on the same side of tissue 60 as the distal end 65 of suture passer 55, passenger suture 50 is inserted through one of these suture loops, i.e., closed loop 25 or closed loop 45. The suture relay is then pulled proximally to draw the suture loop containing passenger suture 50 onto the same side of the tissue as the handle side of the suture passer. In this way passenger suture 50 may be pulled through suture passer 55 from its distal end to its proximal end. As such, passenger suture 50 may be drawn through a piece of tissue from its distal side to its proximal side.

It should also be appreciated that, if desired, second suture 30 may include a closed loop at its proximal end, such as the closed loop 75 shown in phantom in FIG. 3.

Figure 5:
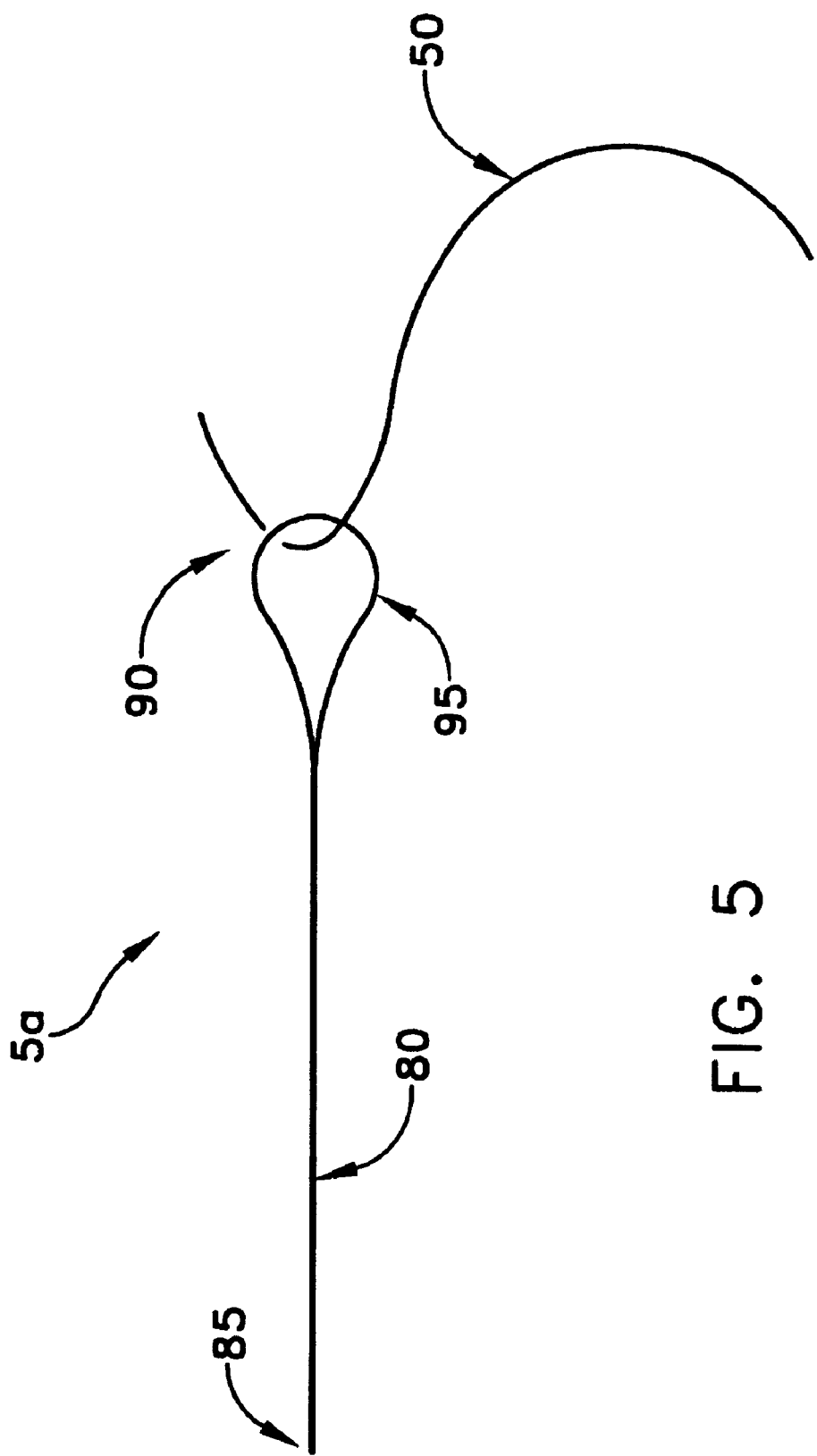
FIG. 5 is a schematic view showing one form of the suture relay, wherein the suture relay comprises a single suture having a closed loop at one end thereof.

Looking now at FIG. 5, there is shown a suture relay 5a which comprises another preferred form of the invention.

Suture relay 5a generally comprises a single suture 80 having a distal end 85 and a proximal end 90, with a closed loop 95 being formed at proximal end 90.

Single suture 80 is formed out of a relatively stiff material, e.g., monofilament suture, such that it may be passed through suture passer 55.

In use, a passenger suture 50 is inserted through closed loop 95 as shown in FIG. 5. Then the distal end 85 of single suture 80 is inserted into the handle side of suture passer 55 and pushed distally, as described above. As this occurs, the passenger suture 50, which is preferably a relatively limp structure such as braided suture, is pulled through the suture passer and hence through the tissue. In this way a relatively limp braided suture may be passed through a hollow suture passer and hence through a piece of tissue.

Having described preferred embodiments of the invention with reference to the accompanying drawings, it is to be understood that the embodiments shown herein are by way of example, and that various changes and modifications may be effected by one skilled in the art without departing from the scope or spirit of the invention as defined in the following claims.

What is claimed is:

1. A surgical assembly comprising:
   a suture relay for use in surgery to transport a passenger suture across tissue, comprising:
     a first suture with a first closed loop at the proximal end of said first suture; and
     a second suture with a second closed loop at the distal end of said second suture;
     wherein said first closed loop of said first suture is engaged with said second closed loop of said second suture.

2. A surgical assembly according to claim 1 wherein said first suture comprises monofilament suture.

3. A surgical assembly according to claim 1 wherein said second suture comprises monofilament suture.

4. A surgical assembly according to claim 1 wherein a passenger suture is passed through one of the group consisting of said first closed loop and said second closed loop.

5. A surgical assembly according to claim 4 wherein said passenger suture comprises braided suture.

6. A surgical assembly according to claim 1 wherein said second suture comprises a third closed loop at said proximal end of said second suture.

7. A surgical assembly according to claim 6 wherein said passenger suture is passed through one of the group consisting of said first closed loop, said second closed loop and said third closed loop.

8. A surgical assembly according to claim 1 wherein said first suture comprises a stiff non-monofilament suture.

9. A surgical assembly according to claim 1 wherein said second suture comprises a stiff non-monofilament suture.

10. A surgical assembly according to claim 1 wherein said first suture comprises a stiffened braided suture.

11. A surgical assembly according to claim 1 wherein said second suture comprises a stiffened braided suture.

12. A method for passing braided suture through soft tissue using suture passer, said method comprising the steps of:

providing a suture relay comprising a first suture with a first closed loop at the proximal end of said first suture, and a second suture with a second closed loop at the distal end of said second suture, wherein said first closed loop of said first suture is engaged with said second closed loop of said second suture;

passing said braided suture through one of the group consisting of said first closed loop and said second closed loop, and passing the suture passer through the soft tissue; and passing said suture relay through said suture passer so as to draw said braided suture through said tissue.

* * * * *